United States Patent
Williams et al.

(10) Patent No.: US 9,429,546 B2
(45) Date of Patent: Aug. 30, 2016

(54) PHASED ARRAY ULTRASONIC BOLT INSPECTION APPARATUS AND METHOD

(71) Applicant: Siemens Energy, Inc., Orlando, FL (US)

(72) Inventors: Jason E. Williams, Cocoa, FL (US); Thomas F. Quinn, Winter Springs, FL (US); Derrick Marcantel, Oviedo, FL (US); Zafir A. M. Abdo, Orlando, FL (US)

(73) Assignee: Siemens Energy, Inc., Orlando, FL (US)

( * ) Notice: Subject to any disclaimer, the term of this patent is extended or adjusted under 35 U.S.C. 154(b) by 396 days.

(21) Appl. No.: 14/222,808

(22) Filed: Mar. 24, 2014

(65) Prior Publication Data
US 2014/0283612 A1    Sep. 25, 2014

Related U.S. Application Data

(60) Provisional application No. 61/804,239, filed on Mar. 22, 2013.

(51) Int. Cl.
*G01N 25/04* (2006.01)
*G01L 5/24* (2006.01)
*G01N 29/24* (2006.01)
*G01N 29/04* (2006.01)
*G01N 29/26* (2006.01)

(52) U.S. Cl.
CPC ............ *G01N 29/24* (2013.01); *G01N 29/043* (2013.01); *G01N 29/262* (2013.01); *G01N 2291/2626* (2013.01); *G01N 2291/2693* (2013.01)

(58) Field of Classification Search
CPC ..................... G01N 25/04; G01N 2291/2691; G01L 5/24
USPC ......................................................... 73/633
See application file for complete search history.

(56) References Cited

U.S. PATENT DOCUMENTS

| | | | | |
|---|---|---|---|---|
| 3,810,385 A | * | 5/1974 | McFaul | G01L 5/246 310/327 |
| 3,977,236 A | * | 8/1976 | Raatz, Jr. | G01N 29/0645 73/614 |
| 4,014,208 A | * | 3/1977 | Moore | G01L 5/246 73/610 |
| 5,131,276 A | * | 7/1992 | Kibblewhite | B06B 1/0662 29/595 |
| 5,156,050 A | * | 10/1992 | Schmid | B06B 1/0681 73/628 |
| 5,205,176 A | * | 4/1993 | Kibblewhite | B06B 1/0662 204/192.15 |
| 5,220,839 A | * | 6/1993 | Kibblewhite | B06B 1/0662 73/761 |
| 5,970,798 A | * | 10/1999 | Gleman | G01L 5/246 73/761 |

(Continued)

FOREIGN PATENT DOCUMENTS

FR      2970567 A1 *  7/2012  ............ G01L 1/255

*Primary Examiner* — Lisa Caputo
*Assistant Examiner* — Jamel Williams (57) ABSTRACT

Ultrasonic bolt inspection apparatus and methods facilitate in situ as well as bench non-destructive evaluation (NDE) inspection of fastening bolt distal ends and their mating nuts. The apparatus is coupled to an exposed end of a fastener bolt head, its exposed thread tip or to a mating nut. The apparatus retains a phased array ultrasonic probe that generates inspection scan data and a rotational position encoder that generates rotational position data. The probe is coupled to an ultrasonic inspection system analyzer, which converts scan data into inspection data that characterizes possible defects in the inspected bolt. A system controller is coupled to the analyzer and the rotational position encoder, correlating rotation position data and inspection data, in order to identify location and characteristics of possible defects in the inspected bolt end.

20 Claims, 6 Drawing Sheets

(56) References Cited

U.S. PATENT DOCUMENTS

| | | | | |
|---|---|---|---|---|
| 6,501,211 | B1* | 12/2002 | Nasrollahzadeh | H01L 41/042 310/317 |
| 6,581,472 | B2* | 6/2003 | Schneider | B25B 23/14 73/597 |
| 6,799,480 | B1* | 10/2004 | Walsh | B25B 23/1427 73/862.21 |
| 8,839,674 | B2* | 9/2014 | Jones | G01N 29/043 73/641 |
| 9,026,379 | B2* | 5/2015 | Chu | G01L 5/24 702/41 |
| 9,127,998 | B1* | 9/2015 | Guldiken | G01L 5/246 |
| 2004/0020296 | A1* | 2/2004 | Moles | G01N 29/0609 73/627 |
| 2005/0022602 | A1* | 2/2005 | Falsetti | G01N 29/11 73/627 |
| 2005/0208452 | A1* | 9/2005 | Lang | A61C 19/04 433/173 |
| 2009/0183572 | A1* | 7/2009 | Zendehroud | F16B 31/025 73/597 |
| 2011/0185864 | A1* | 8/2011 | Ide | G01L 5/24 81/479 |
| 2011/0247434 | A1* | 10/2011 | Carlin | G01L 5/24 73/862.21 |
| 2014/0260628 | A1* | 9/2014 | Devlin | G01N 29/043 73/620 |
| 2014/0260652 | A1* | 9/2014 | Hsieh | F16B 31/02 73/761 |
| 2014/0360281 | A1* | 12/2014 | Helbig | G01B 7/00 73/778 |

* cited by examiner

PHASED ARRAY ULTRASONIC BOLT INSPECTION APPARATUS AND METHOD

CROSS-REFERENCE TO RELATED APPLICATIONS

This application claims the benefit of priority of U.S. provisional patent application entitled "Phased Array Bolt Inspection Rig" filed Mar. 22, 2013 and assigned Ser. No. 61/804,239, the entire contents of which is incorporated by reference herein.

BACKGROUND OF THE INVENTION

1. Field of the Invention

The invention relates to methods and apparatus for performing non-destructive evaluation (NDE) of fastening bolt distal ends and their mating nuts. The bolt distal ends include the bolt head and male threaded bolt tip. The corresponding female threaded nuts engage the male threaded bolt tip. The invention also relates to methods and apparatus for performing NDE of a mated, engaged threaded bolt tip and nut, including in situ NDE within apparatus. In more specific exemplary applications, embodiments of the invention relate to NDE of turbine engine turbine bolts. In embodiments described herein the NDE modality is phased array ultrasonic inspection in either contact or immersion inspection modes.

2. Description of the Prior Art

Figure 1:
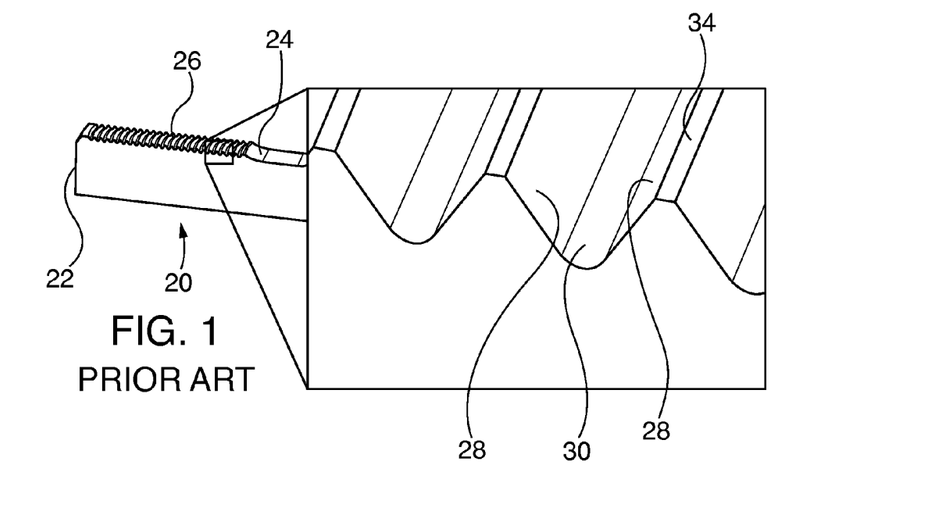
FIG. 1 is a perspective quarter sectional view of a known turbine engine rotor thru-bolt fastener thread side surfaces between the thread root and crest that are inspected embodiments of the ultrasonic inspection system in accordance with embodiments of the invention.
Figure 2:
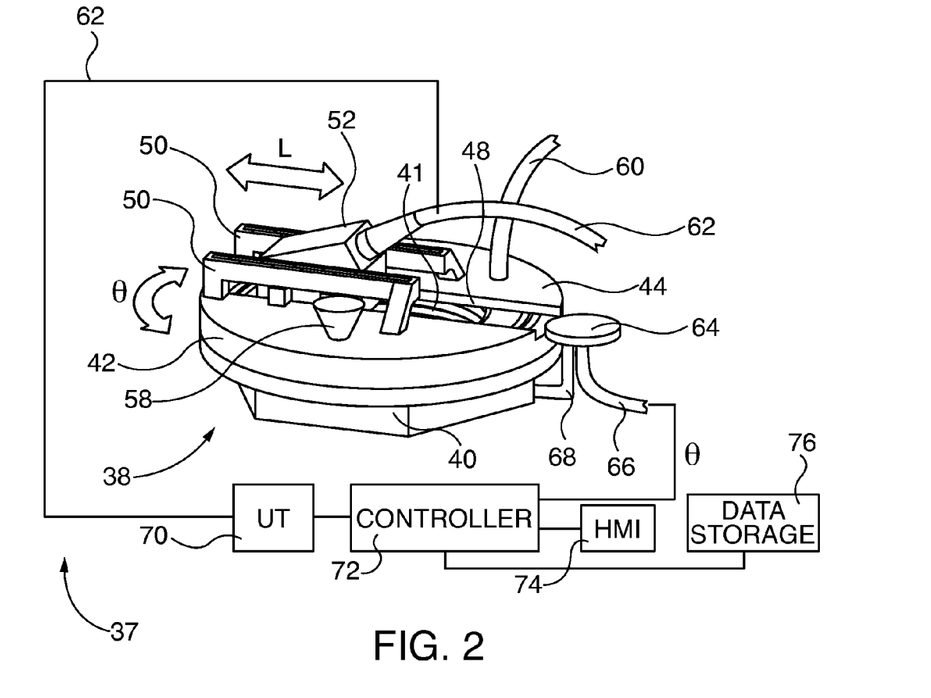
FIG. 2 is a perspective view of a bolt threaded tip ultrasonic inspection apparatus, in accordance with an embodiment of the invention.
Figure 3:
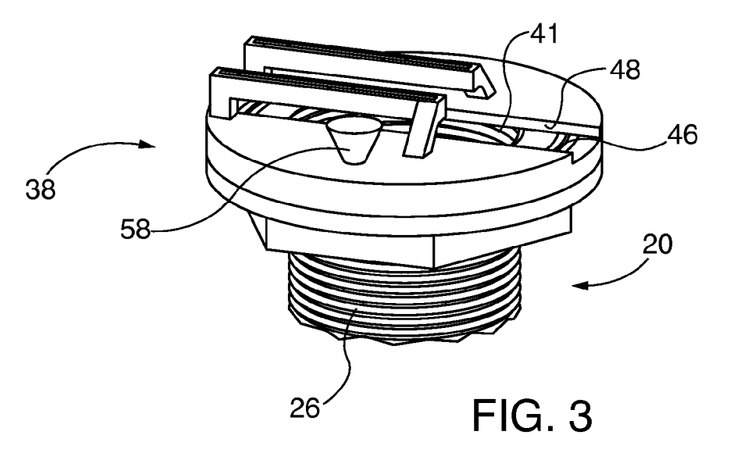
FIG. 3 is a perspective view of the bolt retaining fixture of the apparatus of FIG. 2 attached to a threaded bolt tip.
Figure 7:
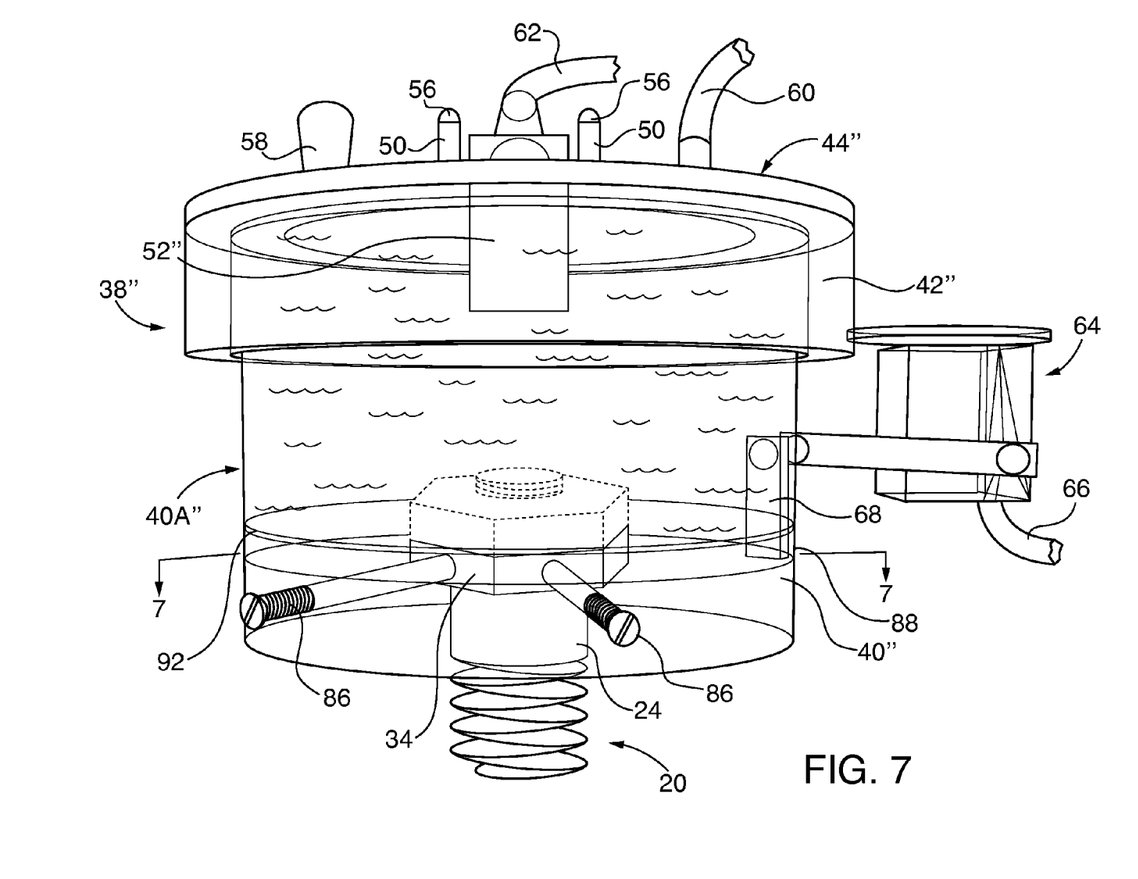
FIG. 7 is a perspective view of an immersion ultrasonic inspection apparatus suitable for inspection of a bolt head or bolt tip/nut interface, in accordance with an embodiment of the invention.

Machinery, such as turbine engines incorporate threaded fasteners that are subject to stress and strain forces during machinery operation. FIG. 1 shows an exemplary quarter sectional, perspective view of a known turbine engine rotor thru-bolt 20 threaded bolt tip 22 and reduced diameter bolt shank 24. The enlarged view portion shows male bolt threads 26 and fastener thread side faces 28 that are defined between the thread roots 30 and thread crest 32. The bolt tip 22 threads 26 are adapted for mating engagement with a female threaded nut. The opposite distal end of the bolt 20 defines a bolt head. Exemplary known bolt head 34 and bolt nut 36 are shown in FIG. 7. It is desirable to inspect fastener threads for defects prior initial service use and/or during subsequent maintenance prior to continued service use. Particularly it is difficult to inspect critical threads in bolt tips or mating nuts at equipment field sites—especially if the fasteners are in situ within the machinery, such as within turbine engine rotors.

Generally cracks in the fastener threaded side face 28 area are very difficult to detect with current methods, especially in field sites. Known methods require human hand held visual or ultrasonic inspection. These known inspection methods are subject to human error during the inspection process as well as variations in the inspection quality by different service personnel. These variations in inspection processes increase potential for unnoticed or missed defects, as well as false identification of non-existent defects. Hand held ultrasonic inspection methods by holding an inspection probe relative to the fastener do not insure consistent scan angles, uniform pressure contact, or signal uniformity as the probe is maneuvered around the fastener. Lack of uniform pressure and consistent orientation during scan maneuvering causes scan signal variations that are not attributable to the fastener physical structure. Contact-type ultrasonic inspection is not successful if the fastener surface is rough or inconsistent. Additionally hand held ultrasonic inspection probes do not assure consistent physical maneuvering of the probe about the fastener or provide probe positional information (e.g., by a position encoder) that can be paired with the scan data for potential fastener 3-D modeling or archiving of scan defect/positional data. The aforementioned challenges to performing NDE ultrasonic inspection of bolt/nut fasteners are even more challenging when attempting to perform an in situ inspection of fasteners installed in machinery, such as turbine engine rotors.

SUMMARY OF THE INVENTION

Phased array ultrasonic bolt inspection apparatus and methods in the embodiments of the invention described herein facilitate NDE inspection of fastening bolt distal ends and their mating nuts. The bolt distal ends include the bolt head and male threaded bolt tip. The corresponding female threaded nut engages the male threaded bolt tip. Embodiments described herein facilitate in situ as well as bench NDE inspection of bolt distal ends and mating nuts. The apparatus is coupled to an exposed end of a fastener bolt head, its exposed thread tip or to a mating nut. The apparatus retains a phased array ultrasonic probe that is coupled to an ultrasonic inspection system, including an ultrasonic analyzer that generates inspection data derived from probe scan data, and a controller. The bolt inspection apparatus enables indexed rotation of the probe on a transducer plate relative to the examined bolt fastener, by having a rotational axis aligned with the axial centerline of the inspected bolt. Rotational position orientation data are captured by an encoder, for processing by the controller along with probe scan data. Embodiments of the apparatus facilitate application of ultrasound inspection liquid couplant between the probe (and probe with alignment wedge) and the inspected surface, allowing inspection of roughened or inconsistent fastener surfaces. Other embodiments provide for immersion ultrasound inspection of an inspected fastener.

Embodiments described herein feature an ultrasonic non-destructive evaluation (NDE) inspection apparatus for a fastening bolt, with a bolt holding fixture adapted for coupling to an end of a bolt about the bolt circumference, for retaining the bolt during an ultrasonic inspection. A transducer plate is rotatively mounted on the holding fixture, having an axis of rotation aligned with an axial centerline of the bolt that is coupled to the holding fixture. A phased array ultrasound probe is coupled to the transducer plate. The probe has a scanning axis intersecting the bolt circumference when the bolt is coupled to the holding fixture.

Other embodiments described herein feature an ultrasonic non-destructive evaluation (NDE) inspection system for a fastening bolt. The system includes a bolt inspection apparatus, having a bolt holding fixture that is adapted for coupling to an end of a bolt about the bolt circumference, for retaining the bolt during an ultrasonic inspection. A transducer plate is rotatively mounted on the holding fixture, and has an axis of rotation aligned with an axial centerline of the inspected bolt. A phased array ultrasound probe is coupled to the transducer plate, having a scanning axis intersecting the bolt circumference when the bolt is coupled to the holding fixture. The probe generates bolt inspection scan data. A rotational position encoder is coupled to the transducer plate, for generating transducer plate rotation position data. An ultrasound analyzer is coupled to the phased array probe, for receiving scan from the probe and for generating inspection data for identifying possible defects in the inspected bolt end. A controller is coupled to the rotational position encoder and the ultrasound analyzer, for receiving and correlating rotation position data and inspection data, in order to identify location and characteristics of possible defects in the inspected bolt end.

Additional embodiments described herein feature a method for non-destructive evaluation of an end of a fastening bolt, by providing an ultrasonic non-destructive evaluation (NDE) inspection system for a fastening bolt, having bolt inspection apparatus. The bolt inspection apparatus has a bolt holding fixture adapted for coupling to an end of a bolt about the bolt circumference, for retaining the bolt during an ultrasonic inspection. The inspection system also has a transducer plate rotatively mounted on the holding fixture, with an axis of rotation aligned with an axial centerline of a bolt coupled to the holding fixture. A phased array ultrasound probe is coupled to the transducer plate, having a scanning axis intersecting the bolt circumference when the bolt is coupled to the holding fixture. The probe generates bolt inspection scan data. A rotational position encoder is coupled to the transducer plate, for generating transducer plate rotation position data. An ultrasound analyzer is coupled to the phased array probe for receiving scan from the probe and generating inspection analysis data for identifying possible defects in an inspected bolt end that is coupled to the holding fixture. The provided system also has a controller coupled to the rotational position encoder and the ultrasound analyzer, for receiving and correlating rotation position data and inspection data, in order to identify location and characteristics of possible defects in the inspected bolt end. The method is further performed by inserting and coupling an end of a bolt into the bolt holding fixture. The transducer plate is rotated, while obtaining bolt inspection scan data with the probe and position data with the rotational position encoder. Inspection analysis data is generated with the ultrasound analyzer, derived from the inspection scan data. The controller then identifies location and characteristics of possible defects in the inspected bolt end, derived from the inspection analysis data and the position data.

The respective objects features of embodiments of the present invention may be applied jointly or severally in any combination or sub-combination by those skilled in the art.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

After considering the following description, those skilled in the art will clearly realize that embodiments of the invention can be readily utilized in phased array ultrasonic bolt inspection apparatus and methods. Embodiments of the invention described herein facilitate NDE inspection of fastening bolt distal ends and their mating nuts. The bolt distal ends include the bolt head and male threaded bolt tip. The corresponding female threaded nuts engage the male threaded bolt tip. Embodiments described herein facilitate in situ as well as bench NDE inspection of bolt distal ends and mating nuts. The apparatus is coupled to an exposed end of a fastener bolt head, its exposed thread tip or to a mating nut. The apparatus retains a phased array ultrasonic probe that is coupled to an ultrasonic inspection analyzer that generates inspection data derived from probe scan data. The analyzer is coupled to a system controller. The apparatus enables indexed relative rotation of the probe and examined fastener, with rotation orientation data captured by an encoder, for processing by the system controller along with analyzer inspection data. Embodiments of the apparatus facilitate application of ultrasound inspection liquid couplant between the probe (and probe with alignment wedge) and the inspected surface, allowing inspection of roughened or inconsistent fastener surfaces. Other embodiments provide for immersion ultrasound inspection of an inspected fastener.

A male bolt thread inspection system 37, which includes an inspection apparatus or fixture 38 for capturing a male threaded end 26 of a fastener bolt 20, is shown in FIGS. 2-5. The inspection fixture 38 has a fastener holding fixture 40, with a base 40A that defines female threads 41 for mating engagement with the bolt male threaded end 26. Upon engagement the bolt 20 is indexed in a fixed rotational position relative to the holding fixture 40, with the bolt axial center line perpendicular to the inspection apparatus or fixture 38. Ring 42 and transducer plate 44 rotate relative to the holding fixture base 40A on annular bearing race 46, with the transducer plate rotational axis aligned with the bolt 20 axial center line. Transducer channel 48 is defined within the transducer plate 46, for generally radial translation of a phased array ultrasonic probe or transducer 52 and contact wedge block 54.

Figure 4:
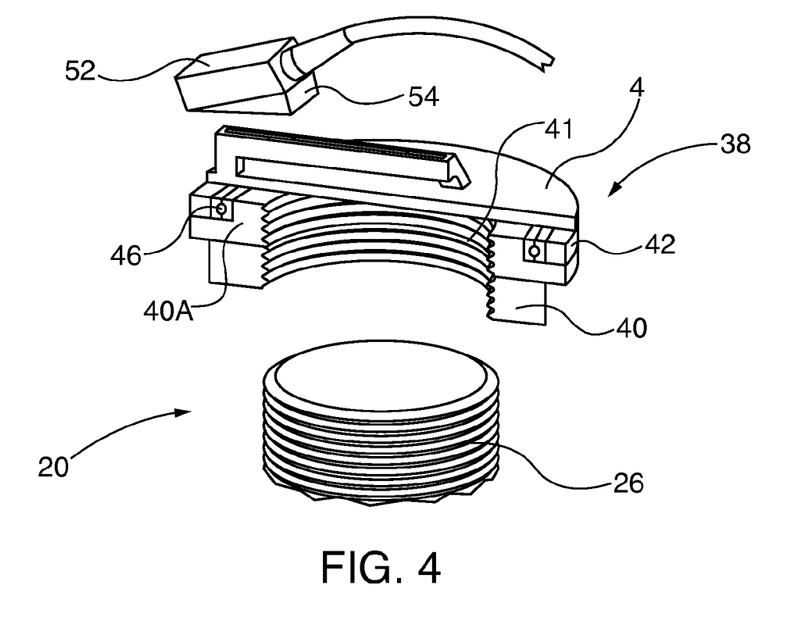
FIGS. 4 and 5 are partially exploded, cross sectional perspective views of the bolt retaining fixture of FIG. 1, showing translation motion of an inspection probe and wedge block for inspection of threads along the axial length of the bolt.
Figure 5:
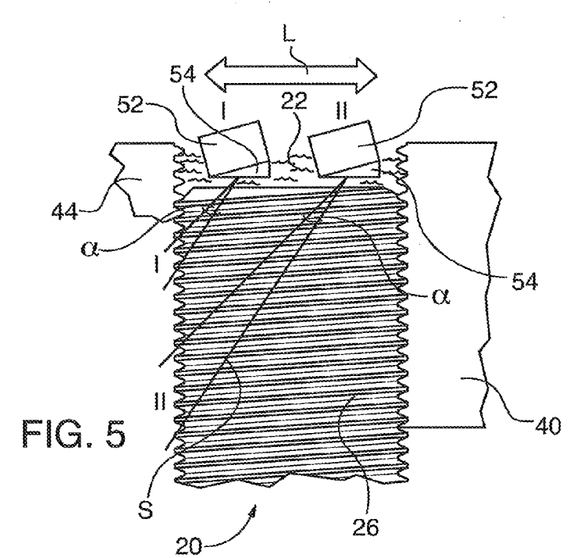

As shown in FIG. 4, radial translation of a known construction phased array probe 52/wedge block 54 in the direction L shifts the scanning beam S of angular width a up and down the axial length of the bolt threads 26, facilitating selective axial placement of the scanning beam at any desired location along the bolt 20, within the holding fixture permitted range of motion. For example in probe position $L_I$ the probe 52 scans the distal tip region I, whereas in position $L_{II}$ the probe scans a lower axial region II. Transducer mounting rails 50 flank the transducer channel 48 and receive transducer mounting screws 56, for selectively fixing the probe translation position L. Rotation knob 58 is coupled to the rotatively mounted transducer plate 44, for selective rotation of the probe 52 relative to the inspected bolt 20 circumference, as indicted by the rotational arrow θ. Liquid couplant of low viscosity, such as water, or higher viscosity ultrasonic gel couplant is desirably introduced between the contact probe wedge block 54 and the bolt tip 22. A liquid couplant supply line 60 facilitates introduction of liquid couplant within the inspection fixture 38.

Transducer cable 62 provides scan beam transmission power to the known construction ultrasonic probe 52 and transfers probe scan data to the rest of the inspection system 37. Rotary position encoder 64 of known design, such as a wheel-type encoder, transfers probe rotational position θ data to the rest of the inspection system 37 via encoder communication cable 66. The encoder 64 is coupled to the inspection fixture 38 by encoder mount 68. Ultrasound analyzer 70 of known construction generates inspection data based on scan data received from the ultrasonic probe 52 by way of the transducer cable 62. Inspection data identify possible defects in the inspected bolt end. System controller 72 is communicatively coupled to the ultrasound analyzer 70 and also the encoder 64 by encoder communication cable 66. The controller 72 receives and correlates rotary position data and the inspection data, in order to identify location and characteristic of possible defects in the inspected bolt end. Embodiments of the controller can utilize known image construction software to construct 3-D models of the inspected bolt end, or otherwise present inspection and location data in desired formats, such as on a visual monitor in the human machine interface (HMI) 74 and/or archive such data in a known volatile or nonvolatile data storage device 76, including remotely accessed data storage devices accessible by local area networks or the Internet.

Figure 6:
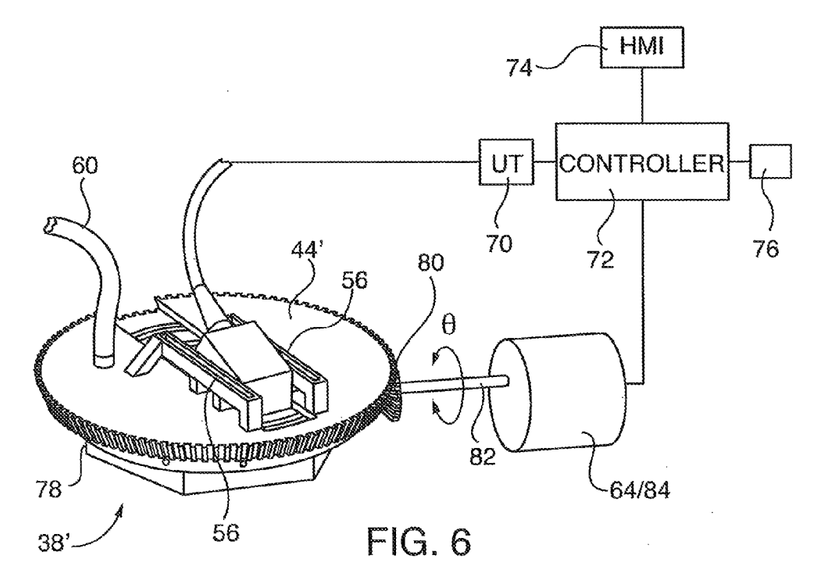
FIG. 6 is a perspective view of a bolt inspection system, including a motorized drive for causing selective rotation of the scanning probe relative to the fastener, in accordance with another embodiment of the invention.

FIG. 6 shows an alternate embodiment inspection system 37', including a motorized inspection fixture 38' that has a motor driven rotatable transducer plate 44', substituting for the manually rotatable transducer plate 44 of FIGS. 2-5. A peripheral ring gear 78 is coupled to the transducer plate 44', which is driven by mating drive pinion 80, drive shaft 82 and drive motor 84. In this embodiment, a rotary position encoder 64 is incorporated in the drive motor 84.

Figure 8:
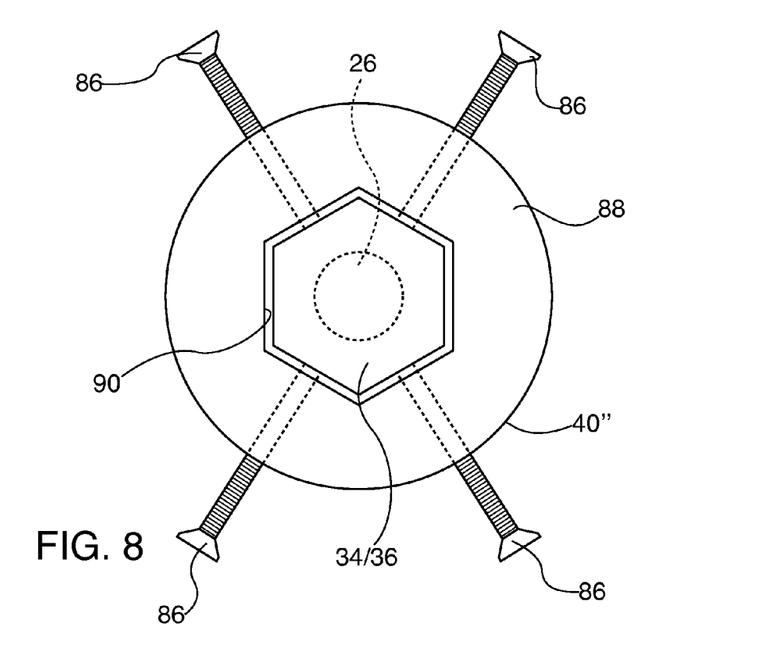
FIG. 8 is a cross sectional plan view of the immersion ultrasonic inspection apparatus of FIG. 7, taken along 8-8 thereof.

An immersion mode phased array ultrasonic inspection fixture embodiment 38" is shown in FIGS. 7 and 8. It is suitable for NDE inspection of non-threaded ends of bolts, namely bolt heads 34 and nuts 36 that are engaged on threaded portions 26 of bolt tips. Known construction phased array immersion probe 52' relies on liquid couplant for propagation of ultrasound waves to the inspected bolt head 34 or the engaged nut 36/bolt threads 26, eliminating the need for direct probe and inspection object abutting contact. Couplant fills the cavity defined by the base 40A", the rotating ring 42" and the transducer plate 44". A flexible retaining bladder 92, such as a flat elastomeric sheet is interposed between the base 40A" and the holding fixture 40", preventing the couplant above the bladder from escaping out of the base. The bladder 92 abuts and contacts the inspected bolt end, assuring satisfactory transmission of ultrasonic inspection waves from and to the probe 52".

As shown in FIG. 8, the holding fixture 40" includes a plurality of tension screws 86 that collectively clamp and capture circumferential edges of the inspected bolt end bolt head 34 or nut 36. Centering fixture 88 centers the inspected bolt axial centerline axis with the transducer plate 44" by circumscribing the inspected bolt in a centering fixture cutout 90 that has a profile conforming to the head 34 or nut 36 circumferential profile. Centering fixtures 88 are removable from the inspection fixture 38", so that a cutout 90 profile is chosen to match that of the inspected bolt end.

Figure 9:
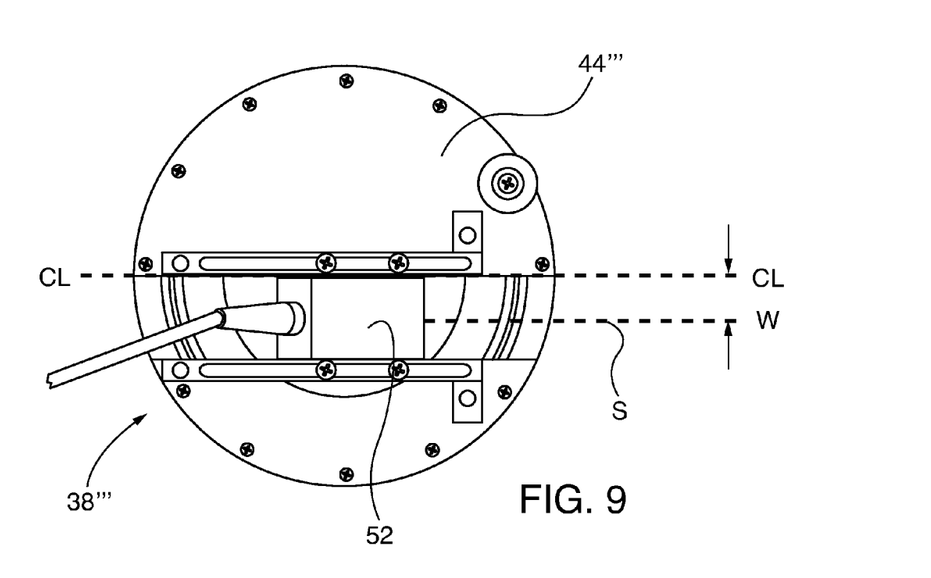
FIG. 9 is a top plan view of another embodiment of a bolt threaded tip ultrasonic inspection apparatus, having a laterally offset inspection probe, in accordance with another embodiment of the invention.
Figure 10:
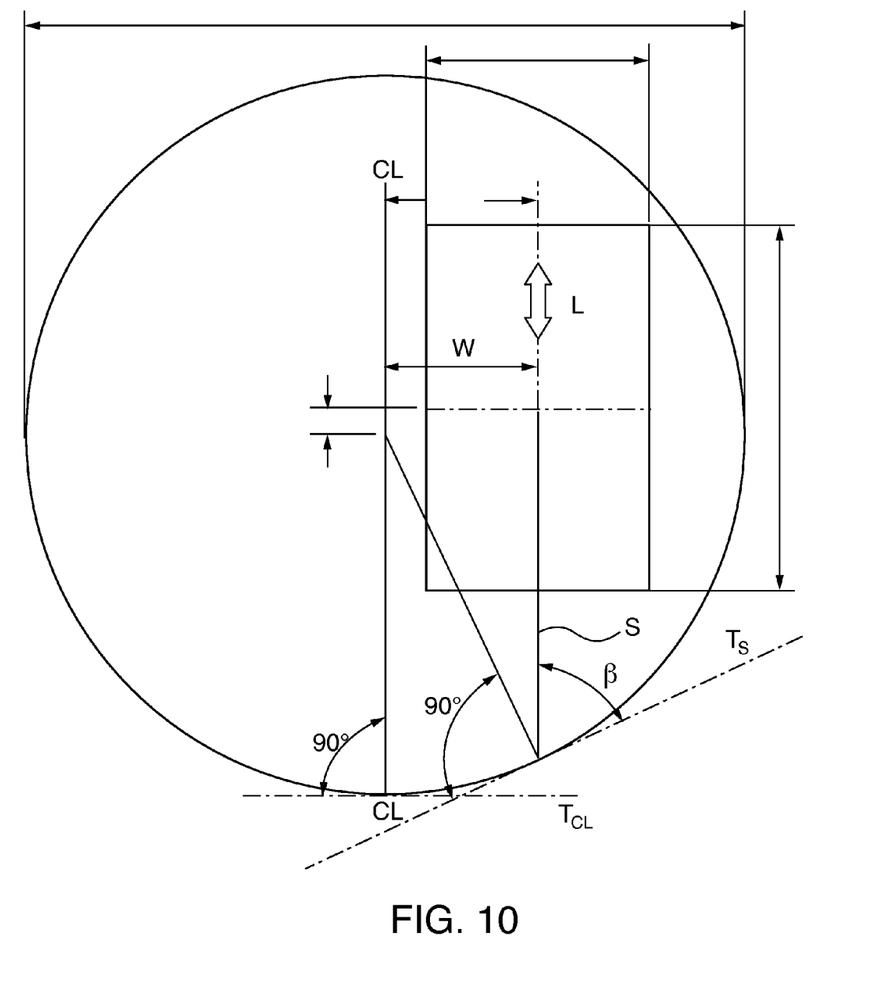
FIG. 10 is a schematic planar view of phased array scanning geometry of the inspection apparatus of FIG. 9, which facilitates inspection of fastener thread side surfaces between the thread root and crest.

For some NDE applications it is preferable that the ultrasonic probe be mounted on the transducer plate in an offset fashion so that the probe scan centerline intersects a tangential surface of the inspected bolt end at a skewed angle greater or less than 90 degrees. Skewed scan angles are beneficial for inspection of thread side faces 28 shown in FIG. 1, by directing the scan beam angle to intersect the thread side face at a generally normal angle; so that the incident and reflected scan pulse waves are less subject to interference by surrounding structure in the scanned object. FIGS. 9 and 10 show an inspection fixture 38' wherein the contact probe 52 scan line S is offset a lateral distance W from the transducer plate 44' rotational axis centerline CL. The offset probe 52 scan line S intersects a tangent $T_S$ to the inspected surface at an angle β, rather than normal to the surface tangent $T_{CL}$ as if the probe scan axis was aligned with the transducer plate rotational axis centerline CL. The scan angle β can be varied selectively by varying the offset W of the probe scan line S. To this end, the transducer plate 44''' can be modified to provide for laterally adjustable offset W for the probe 52.

It is noted that any given inspection fixture can be reconfigured with any of the holding fixture 40, 40', 40" embodiments that may be suitable for any given NDE inspection task. All of these described holding fixtures are suitable for in situ inspection of bolt heads that are installed in machinery, as the entire inspection fixture 38, 38', 38" and 38' have compact peripheral profiles suitable for insertion into confined spaces within machinery. For example the inspection fixture is insertable between rotor discs of a turbine engine and thus may be utilized for NDE inspection of rotor mounted thru-bolt heads, threaded tips and bolt tip/retaining nut interfaces.

Although various embodiments that incorporate the teachings of the present invention have been shown and described in detail herein, those skilled in the art can readily devise many other varied embodiments that still incorporate these teachings. The invention is not limited in its application to the exemplary embodiment details of construction and the arrangement of components set forth in the description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

What is claimed is:

1. An ultrasonic non-destructive evaluation (NDE) inspection apparatus for a fastening bolt, comprising:

a bolt holding fixture adapted for coupling to an end of a bolt about the bolt circumference, for retaining the bolt during an ultrasonic inspection;

a transducer plate rotatively mounted on the holding fixture, having an axis of rotation aligned with an axial centerline of a bolt coupled to the holding fixture; and a phased array ultrasound probe coupled to the transducer plate, having a scanning axis intersecting the bolt circumference when the bolt is coupled to the holding fixture.

2. The apparatus of claim 1, the holding fixture further comprising female threads adapted for coupling engagement with male threads of a bolt tip, for retaining the bolt during an ultrasonic inspection.

3. The apparatus of claim 1, the holding fixture further comprising a cutout conforming to circumferential profile of a bolt head or nut, for retaining the bolt head or nut therein during an ultrasonic inspection.

4. The apparatus of claim 1, the holding fixture further comprising radially inwardly-oriented tension screws adapted for clamping engagement with a circumferential profile of a bolt head or nut, for retaining the bolt during an ultrasonic inspection.

5. The apparatus of claim 1, further comprising a couplant supply line for introducing ultrasonic couplant between the bolt end and the probe during NDE inspection of a bolt end.

6. The apparatus of claim 1 the transducer plate defining a transducer channel adapted for selective translation of the probe scanning axis along axial length of a bolt during an ultrasonic inspection of a bolt that is retained in the holding fixture.

7. The apparatus of claim 6, the transducer channel oriented for laterally offset alignment of the probe scanning axis relative to the transducer plate rotational axis.

8. The apparatus of claim 1, the probe scanning axis oriented in laterally offset alignment relative to the transducer plate rotational axis.

9. The apparatus of claim 1 further comprising a rotational position encoder coupled to the transducer plate, for generating transducer plate rotation position data.

10. The apparatus of claim 1, the bolt holding fixture having a couplant retaining bladder interposed between the probe and an end of a bolt retained in the holding fixture, for retaining couplant around the probe.

11. The apparatus of claim 1, further comprising a drive system coupled to the transducer plate, for selectively rotating the probe during an NDE inspection.

12. An ultrasonic non-destructive evaluation (NDE) inspection system for a fastening bolt, comprising:
a bolt inspection apparatus, having:
a bolt holding fixture adapted for coupling to an end of a bolt about the bolt circumference, for retaining the bolt during an ultrasonic inspection;
a transducer plate rotatively mounted on the holding fixture, having an axis of rotation aligned with an axial centerline of a bolt coupled to the holding fixture; and
a phased array ultrasound probe coupled to the transducer plate, having a scanning axis intersecting the bolt circumference when the bolt is coupled to the holding fixture, the probe generating bolt inspection scan data;
a rotational position encoder coupled to the transducer plate, for generating transducer plate rotation position data;
an ultrasound analyzer coupled to the phased array probe for receiving scan from the probe and generating inspection data for identifying possible defects in an inspected bolt end that is coupled to the holding fixture; and
a controller coupled to the rotational position encoder and the ultrasound analyzer, for receiving and correlating rotation position data and inspection data, in order to identify location and characteristics of possible defects in the inspected bolt end.

13. The system of claim 12, the bolt holding fixture further comprising female threads adapted for coupling engagement with male threads of a bolt tip or a cutout conforming to circumferential profile of a bolt head or nut, for retaining the bolt during an ultrasonic inspection.

14. The system of claim 12, further comprising the transducer plate defining a transducer channel adapted for selective translation of the probe scanning axis along axial length of a bolt during an ultrasonic inspection of a bolt that is retained in the holding fixture.

15. The system of claim 10, the bolt holding fixture having a couplant retaining bladder interposed between the probe and an end of a bolt retained in the holding fixture, for retaining couplant around the probe.

16. The system of claim 12, further comprising a drive system coupled to the transducer plate and the controller, for selectively rotating the probe during an NDE inspection.

17. A method for non-destructive evaluation of an end of a fastening bolt, comprising:
providing an ultrasonic non-destructive evaluation (NDE) inspection system for a fastening bolt, comprising:
a bolt inspection apparatus, having:
a bolt holding fixture adapted for coupling to an end of a bolt about the bolt circumference, for retaining the bolt during an ultrasonic inspection;
a transducer plate rotatively mounted on the holding fixture, having an axis of rotation aligned with an axial centerline of a bolt coupled to the holding fixture; and
a phased array ultrasound probe coupled to the transducer plate, having a scanning axis intersecting the bolt circumference when the bolt is coupled to the holding fixture, the probe generating bolt inspection scan data;
a rotational position encoder coupled to the transducer plate, for generating transducer plate rotation position data;
an ultrasound analyzer coupled to the phased array probe for receiving scan from the probe and generating inspection analysis data for identifying possible defects in an inspected bolt end that is coupled to the holding fixture; and
a controller coupled to the rotational position encoder and the ultrasound analyzer, for receiving and correlating rotation position data and inspection data, in order to identify location and characteristics of possible defects in the inspected bolt end;
inserting and coupling an end of a bolt into the bolt holding fixture;
rotating the transducer plate, while obtaining bolt inspection scan data with the probe and position data with the rotational position encoder;
generating inspection analysis data derived from the inspection scan data with the ultrasound analyzer;
identifying location and characteristics of possible defects in the inspected bolt end, derived from the inspection analysis data and the position data with the controller.

18. The method of claim 17, further comprising:
selectively translating the probe relative to the transducer plates, so that the probe scanning axis intersects different axial positions along the axial length of the bolt circumference during the inspection.

19. The method of claim 18, further comprising laterally offsetting alignment of the probe scanning axis relative to the transducer plate rotational axis, for changing scanning axis alignment relative to a tangent of the bolt circumference.

20. The method of claim 17 further comprising laterally offsetting alignment of the probe scanning axis relative to the transducer plate rotational axis, for changing scanning axis alignment relative to a tangent of the bolt circumference.

* * * * *